United States Patent
Steiger et al.

(10) Patent No.: US 6,863,478 B2
(45) Date of Patent: Mar. 8, 2005

(54) DEVICE FOR CONNECTING SURGICAL CLEARING OR DRILLING TOOL COMPONENTS

(76) Inventors: Peter Steiger, Wysshölzlistrasse 34, Herzogenbuchsee (CH), CH-3360; Peter Brunner, Effingerstrasse 93, Bern (CH), CH-3008

(*) Notice: Subject to any disclaimer, the term of this patent is extended or adjusted under 35 U.S.C. 154(b) by 0 days.

(21) Appl. No.: 10/397,518

(22) Filed: Mar. 27, 2003

(65) Prior Publication Data

US 2004/0024404 A1 Feb. 5, 2004

Related U.S. Application Data

(63) Continuation of application No. PCT/CH00/00527, filed on Sep. 27, 2000.

(51) Int. Cl.[7] ............................................. B23B 51/02
(52) U.S. Cl. .................... 408/226; 76/115; 408/231; 408/239 R; 606/80; 279/104
(58) Field of Search ................................ 279/93, 94, 96, 279/102, 103, 104, 105; 408/226, 238, 239 R, 239 A, 231; 606/79, 80, 180; 403/278, 282, 285, 361; 76/108.1, 108.6, 115

(56) References Cited

U.S. PATENT DOCUMENTS

| 879,631 | A | * | 2/1908 | Gregson | 76/108.1 |
| 3,850,054 | A | * | 11/1974 | Weissman | 76/108.1 |
| 3,952,812 | A | * | 4/1976 | Lucan | 172/375 |
| 5,163,790 | A | * | 11/1992 | Vig | 408/57 |
| 5,167,476 | A | * | 12/1992 | Lafferty et al. | 408/240 |
| 5,499,984 | A | * | 3/1996 | Steiner et al. | 606/80 |
| 5,693,047 | A | | 12/1997 | Meyers et al. | 606/80 |
| 5,720,749 | A | | 2/1998 | Rupp | 606/79 |
| 5,759,185 | A | * | 6/1998 | Grinberg | 606/80 |
| 5,879,353 | A | * | 3/1999 | Terry | 606/85 |
| 6,015,411 | A | * | 1/2000 | Ohkoshi et al. | 606/80 |
| 6,220,417 | B1 | | 4/2001 | Linsbauer | 192/76 |
| 6,572,311 | B2 | * | 6/2003 | Vasudeva | 408/226 |
| 6,689,138 | B2 | * | 2/2004 | Lechot et al. | 606/80 |
| 2002/0009342 | A1 | * | 1/2002 | Vasudeva | 408/226 |

FOREIGN PATENT DOCUMENTS

| DE | 297 13 920 U1 | 10/1997 |
| EP | 0 195 150 A1 | 9/1986 |

* cited by examiner

Primary Examiner—Daniel W. Howell
(74) Attorney, Agent, or Firm—Jones Day

(57) ABSTRACT

A device for the coaxial connection of a surgical rotating tool to a shaft and the method of forming such a device. The device comprises a shaft defining a central axis and having a front end, a hollow body having a first end for engaging the front end of the shaft and a second end for engaging the tool. The hollow body further includes a wall defining a cavity coaxial to the central axis, the wall has at least one deformed impression thereby defining at least one projection in communication with the cavity. The at least one projection is engaged with the shaft to produce a rotatively and axially fixed connection between the shaft and the hollow body.

16 Claims, 2 Drawing Sheets

DEVICE FOR CONNECTING SURGICAL CLEARING OR DRILLING TOOL COMPONENTS

CROSS-REFERENCE TO RELATED APPLICATIONS

This application is a continuation of the U.S. national stage designation of copending International Patent Application PCT/CH00/00527, filed Sep. 27, 2000, the entire content of which is expressly incorporated herein by reference thereto.

FIELD OF THE INVENTION

The invention relates to a device for the connection of surgical clearing or drilling tools to a shaft.

BACKGROUND OF THE INVENTION

In various instruments used in surgery, a transmission of torque or force between two components of the instrument is necessary. The transmission of torque serves, for example, for the rotative drive of a surgical tool while the transmission of force is done in the axial direction. Form-locking connections between the two parts are advantageous for the transmission of torque or force. Such connections occur, for example, in the coupling of a flexible drill shaft with the drilling heads for the boring of marrow spaces in bones.

Such a device with form-locking connections for the transmission of torque and axial force between a drive means and a flexible shaft, as well as between the flexible shaft and a clearing tool, has been disclosed in U.S. Pat. No. 5,720,749 to Rupp. In one embodiment, before the joining of the clearing tool and the flexible shaft through plastic deformation, cams are formed in the cylindrical hollow section of a hollow body on the clearing tool. The hollow body provides axial accommodation for the flexible shaft. Subsequently, the flexible shaft is pressed in the axial direction into the hollow section provided with cams whereby the shaft is radially deformed by the cams and is connected to the hollow body, tangentially by means of a form-lock and axially by means of a press fit. One disadvantage of this connection is that, through the pressing of the flexible shaft into the hollow section with cams, the flexible shaft is significantly deformed by the cams and thus, despite the axial conical centering at the front end, a corresponding concentric coaxial connection is not ensured.

An improved connection is desirably one that preferably provides a form-locking connection for the transmission of torque and axial force in which the joining of the flexible shaft to the hollow body is accomplished, absolutely concentrically and coaxially, by means of a sliding fit in which a rotatively and axially form-locking connection can be produced.

SUMMARY OF THE INVENTION

The present invention is directed to a device for the coaxial connection of a surgical rotating tool to a shaft comprising a shaft defining a central axis and having a front end, a hollow body having a first end for engaging the front end of the shaft and a second end for engaging a tool or coupling. The hollow body further includes a wall defining a cavity coaxial to the central axis, the wall has at least one plastically deformed impression thereby defining at least one projection in communication with the cavity. The at least one projection is engaged with the shaft to produce a rotatively and axially fixed connection between the shaft and the hollow body.

In one embodiment of the device, the shaft is substantially circular cylindrical having a first diameter, the cavity is substantially circular cylindrical having a second diameter, wherein first and second diameters are dimensioned such that a close sliding fit is formed between the shaft and the cavity.

In addition, the engagement of the shaft with the at least one projection upon introduction in the hollow space may elastically deform the shaft. Alternatively the shaft may be both elastically and plastically deformed or the shaft may be entirely plastically deformed. The at least one raised section may have a height measured from the wall to the central axis of 0.05 mm to 0.70 mm.

The device according to the present invention may comprise, in addition, an axial stop further defining the cavity for limiting the introduction of the shaft into the hollow space, the axial stop being at a depth T from the first end. In one embodiment, the wall of the hollow body may have a thickness between 0.1 mm and 1.0 mm.

In another embodiment, a device according to the present invention for the coaxial connection of surgical clearing or drilling tools to a shaft includes a shaft and a hollow body with a hollow space coaxial to the central axis, where the shaft is introduced, by its front end, coaxially into the hollow space, from its first end, and the hollow body can be connected by its second end to an instrument component, for example, a coupling part or a drill head for marrow space drilling. Moreover, the wall of the hollow body has at least one plastically deformable impression with a raised section in the hollow body. In this case, the shaft's deformation caused by the at least one raised section can be a plastic and/or elastic deformation.

In a preferred form of embodiment of the device according to the invention the shaft is structured at the front end as a circular cylinder coaxial to the central axis and has a diameter d. The hollow space is also formed as a circular cylinder coaxial to the central axis and has a diameter D, where the diameters d and D are chosen so that a close sliding fit is formed between the shaft and the hollow space. Through the close sliding fit a precisely coaxial connection between shaft and hollow body is made possible which is not affected by the application of pressing forces during the production of the plastic impressions in the hollow body after pushing in the shaft. Thereby a fixed, axially and tangentially form-locking, connection between the shaft and hollow body can be produced which ensures a concentric rotation of the instrument component.

In an additional form of embodiment of the device according to the invention, the hollow space includes at a depth T measured from the first end an axial stop face for the shaft. Through this axial stop face a securement for the accommodation of large axial pressing forces on the device arises in addition for the axially and tangentially form-locking connection between the shaft and hollow body by means of the impressions.

Preferably the wall thickness of the hollow body is between 0.1 mm and 1.0 mm while the raised sections preferably project between 0.05 mm and 0.70 mm from the wall.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
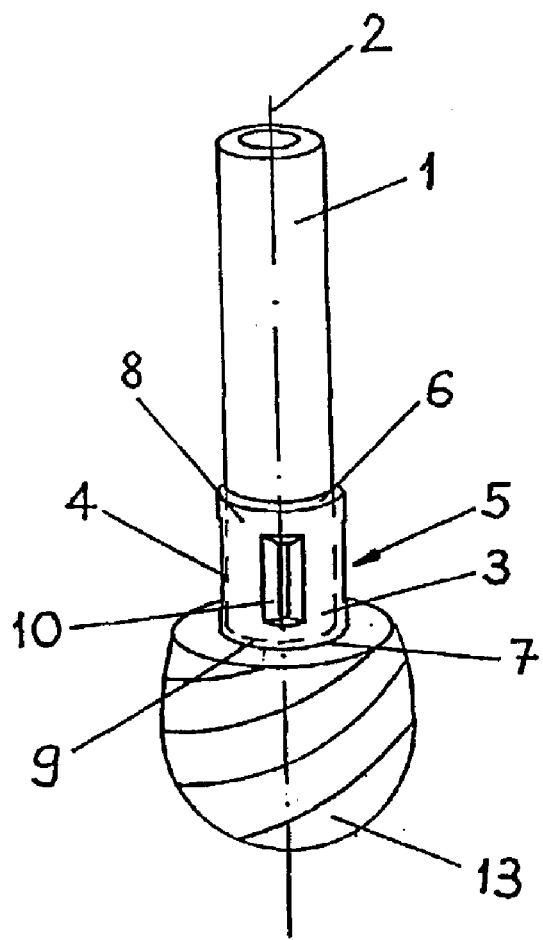
FIG. 1 is a perspective view of a preferred embodiment of the device according to the present invention.
Figure 2:
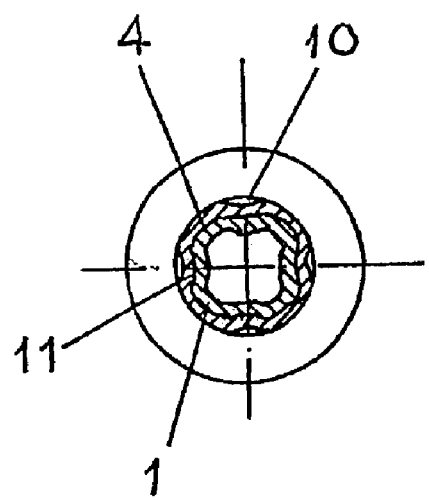
FIG. 2 is a cross-sectional view of the shaft and hollow body of the device shown in FIG. 1.

In FIGS. 1 and 2, a preferred embodiment of the device according to the present invention is represented which includes a hollow body 5 fixedly connected to a surgical drill head 13. The cylindrical shaft 1 coupled to the drive (not shown) is introduced coaxially relative to a central axis 2 into a cylindrical cavity, chamber or hollow space 4 of hollow body 5. The outer diameter of the shaft 1 and the inner diameter of the hollow space 4 form a close sliding fit such that the shaft 1 and hollow body 5 are aligned exactly concentrically and wherein shaft 1 can be introduced into hollow space 4 without the expenditure of force. An axial stop face 9 is introduced at a certain depth of hollow space 4 and transverse to the central axis 2 for limiting the introduction of the shaft into the hollow space 4. In one embodiment, stop face 9 can coincide with the apical surface, on the hollow body-side, of the drill head 13. The hollow body 5 is structured as a hollow cylinder concentric to the central axis 2 and includes on the shaft side a first end 6, on the drill side a second end 7, a wall 8 having outer and inner surfaces to define a hollow space 4 coaxial to the central axis 2. In one embodiment, the wall of the hollow body 5 may have a thickness between 0.1 mm and 1.0 mm. After shaft 1 is introduced coaxially by its front, drill-side end 3 into hollow space 4 at first end 6 of the hollow body 5, the wall 8 of the hollow body 5 is deformed by means of an impressing tool (not shown) such that four impressions 10 arise each of which has a projection or raised section 11 or portion extending into hollow space 4. The impressions 10 are preferably plastically deformed. Through the raised sections 11, shaft 1 is deformed on its circumferential surface in a manner corresponding to the raised sections 11 such that a form-locking fixation with respect to rotation about the central axis 2 and with respect to displacement between the shaft 1 and the hollow body 5 along the central axis 2 is produced. In addition, the engagement of the shaft with the at least one raised section 11 upon introduction in the hollow space 4 may elastically deform the shaft 1. Alternatively the shaft 1 may be both elastically and plastically deformed or the shaft 1 may be entirely plastically deformed. The at least one raised section 11 may have a height measured from the wall to the central axis of 0.05 mm to 0.70 mm. Still referring to FIG. 1, in the embodiment of the device according to the present invention shown here, the hollow body 5 and the drill head 13 are one piece.

Figure 3:
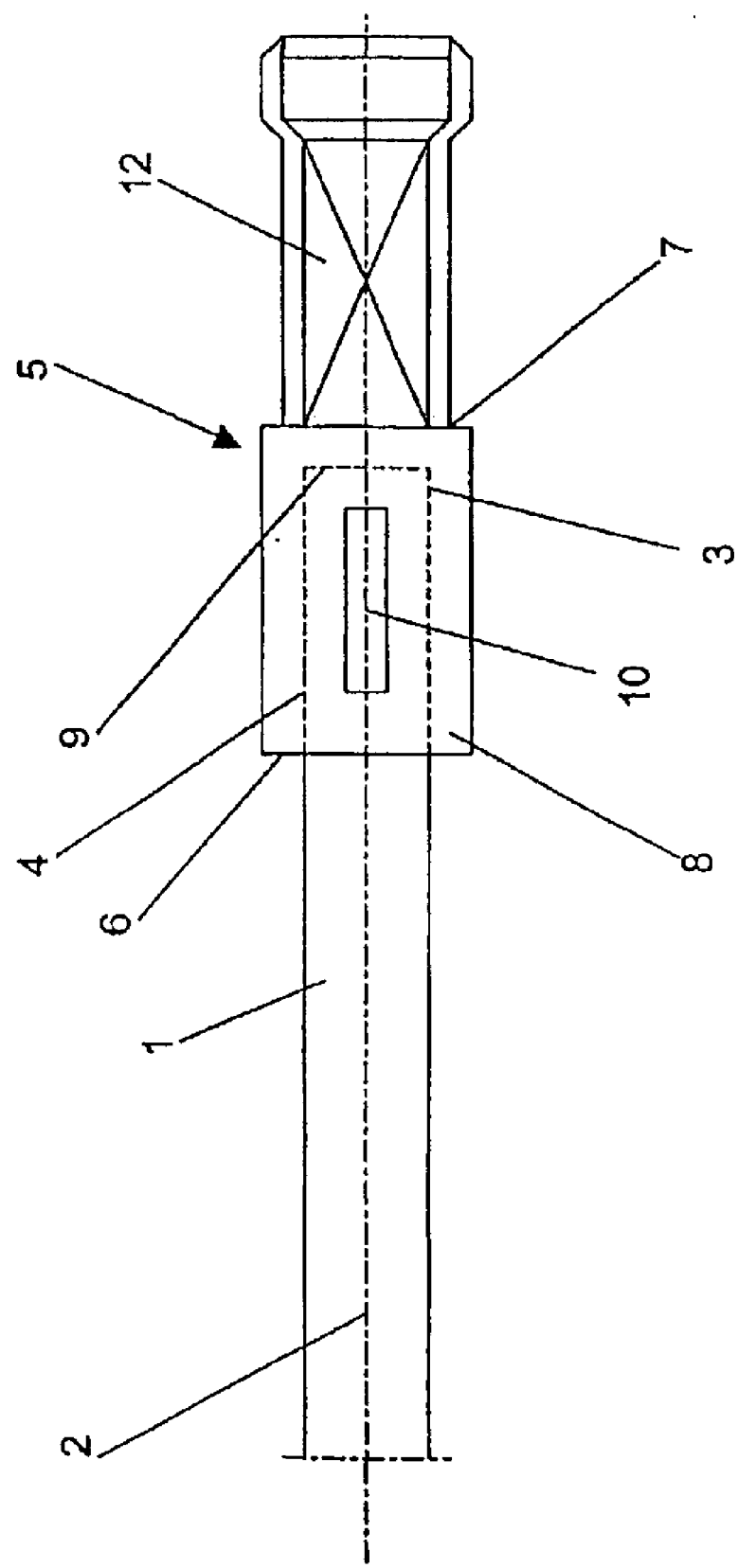
FIG. 3 is a plan view of another preferred embodiment of the device according to the present invention.

Another embodiment of the device according to the present invention shown in FIG. 3 is distinguished from that shown and described in FIG. 1 in that hollow body 5 is connected at its second end 7 axially at a distance from the shaft 1, to a coupling part 12, wherein the coupling part 12 serves for removable connection to a surgical clearing or drilling tool (not shown).

One may appreciate that a fixed connection may be advantageously produced between the shaft 1 and the hollow body 5 with the instrumental component, for example, a coupling part or a drill head for the marrow space. The individual parts of the device according to the invention are simple to manufacture and the connection between the shaft 1 and hollow body 5, which is accomplished by the plastic deformation of the wall after pushing the shaft into the wall, can be produced with the simplest means. Furthermore, smaller shaft diameters as well as a left/right course of the drive machine are possible.

What is claimed is:

1. A device for the coaxial connection of a surgical rotating tool to a shaft comprising:

a shaft extending along a central axis from a front end to a rear end;

a hollow body having a first end for engaging the front end of the shaft and a second end for engaging the tool, the hollow body further having a wall defining a cavity coaxial to the central axis, the wall having at least one plastically deformed impression defining at least one projection in communication with the cavity; and wherein at least one projection is engaged with the shaft to produce a rotatively and axially fixed connection between the shaft and the hollow body: and wherein the shaft is elastically deformed by the at least one projection.

2. The device of claim 1, wherein the shaft is substantially circular cylindrical having a first diameter, the cavity is substantially circular cylindrical having a second diameter, wherein first and second diameters are dimensioned such that a close sliding fit is formed between the shaft and the cavity.

3. A device for the coaxial connection of a surgical rotating tool to a shaft comprising:

a shaft extending along a central axis from a front end to a rear end;

a hollow body having a first end for engaging the front end of the shaft and a second end for engaging the tool, the hollow body further having a wall defining a cavity coaxial to the central axis, the wall having at least one plastically deformed impression defining at least one projection in communication with the cavity; and wherein at least one projection is engaged with the shaft to produce a rotatively and axially fixed connection between the shaft and the hollow body, and wherein the hollow body and the surgical rotating tool are formed integrally.

4. The device of claim 3, wherein the rotating tool is a surgical clearing and drilling tool.

5. The device of claim 1, further comprising an axial stop for limiting the introduction of the shaft into the cavity, the axial stop being at a predetermined depth from the first end.

6. The device of claim 1, wherein the wall of the hollow body has a thickness between 0.1 mm and 1.0 mm.

7. The device of claim 1, wherein the at least one projection has a height of 0.05 mm to 0.70 mm measured from the wall toward the central axis.

8. The device of claim 1, wherein the hollow body and the surgical rotating tool are formed integrally.

9. The device of claim 1, wherein the rotating tool is a surgical clearing and drilling tool.

10. A device for the coaxial connection of a surgical rotating tool to a shaft comprising:

a substantially circular cylindrical member having a first end including a wall, the wall having an outer and inner surface, the inner surface defining a substantially circular cylindrical chamber having a central axis, the cylindrical member further having a second end for coupling to the tool;

a shaft having a front end, the front end slidably engageable with the chamber; and wherein the outer surface of the wall has at least one impression corresponding to at least one projection on the inner surface in communication with the chamber such that the at least one projection engages the front end of the shaft to form a rotatively and axially locking connection between the shaft and the cylindrical member;

wherein the shaft is elastically deformed by the at least one projection; and wherein the substantially circular cylindrical member and the surgical rotating tool are formed integrally.

11. A method of forming a fixed connection of a surgical rotating tool to a shaft, the method comprising the steps of:

providing a shaft having a substantially circular cylindrical front end having a first diameter;

providing a substantially circular cylindrical member having a first end including a wall, the wall having an outer and inner surface, the inner surface defining a substantially circular cylindrical chamber having a central axis and a second diameter, the cylindrical member further having a second end for coupling to the tool;

inserting the front end of the shaft into the chamber, the diameters being dimensioned such that a sliding fit is formed between the shaft and the chamber;

deforming the outer surface of the wall and forming at least one projection on the inner surface of the wall, the projection engaging the front end of the shaft thereby elastically deforming the front end of the shaft to produce a rotatively and axially locking connection between the shaft and the cylindrical member.

12. The device of claim 3, wherein the at least one projection has a height of 0.05 mm to 0.70 mm measured from the wall toward the central axis.

13. The device of claim 3, wherein the shaft is substantially circular cylindrical having a first diameter, the cavity is substantially circular cylindrical having a second diameter, wherein first and second diameters are dimensioned such that a close sliding fit is formed between the shaft and the cavity.

14. The device of claim 3, wherein the shaft is plastically deformed by the at least one projection.

15. The device of claim 3, further comprising an axial stop for limiting the introduction of the shaft into the cavity, the axial stop being at a predetermined depth from the first end.

16. The device of claim 3, wherein the wall of the hollow body has a thickness between 0.1 mm and 1.0 mm.

* * * * *